United States Patent
Sheets, Jr. et al.

(10) Patent No.: US 7,699,191 B2
(45) Date of Patent: Apr. 20, 2010

(54) SURGICAL MULTIPLE USE ADHESIVE APPLIER

(75) Inventors: John W. Sheets, Jr., Bridgewater, NJ (US); Donna L. Korvick, Maineville, OH (US); Georgette A. Belair, West Chester, OH (US); Mark S. Ortiz, Milford, OH (US); Wells D. Haberstich, Loveland, OH (US); Ronald J. Kolata, Cincinnati, OH (US); Frederick E. Shelton, IV, Hillsboro, OH (US); James W. Voegele, Cincinnati, OH (US); Margaret M. D'Aversa, Whitehouse Station, NJ (US); Michael T. Mather, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 582 days.

(21) Appl. No.: 11/558,138

(22) Filed: Nov. 9, 2006

(65) Prior Publication Data
US 2008/0112751 A1 May 15, 2008

(51) Int. Cl.
*B65D 35/22* (2006.01)
*B65D 35/28* (2006.01)
*B65D 47/22* (2006.01)
*B65D 47/36* (2006.01)

(52) U.S. Cl. ............ 222/94; 222/103; 222/541.3; 222/541.4; 401/132; 604/311

(58) Field of Classification Search .......... 222/94, 222/103, 541.3, 541.4; 401/132; 604/214, 604/310, 311
See application file for complete search history.

(56) References Cited

U.S. PATENT DOCUMENTS

| | | | | |
|---|---|---|---|---|
| 3,524,537 A | * | 8/1970 | Winter | 206/229 |
| 4,090,642 A | * | 5/1978 | Baker | 222/94 |
| 4,733,797 A | * | 3/1988 | Haber | 221/8 |
| 5,928,611 A | | 7/1999 | Leung | |
| 6,340,097 B1 | | 1/2002 | D'Alessio et al. | |
| 6,725,857 B2 | * | 4/2004 | Ritsche | 128/200.14 |
| 6,726,665 B1 | * | 4/2004 | Embleton et al. | 604/290 |
| 6,941,948 B2 | * | 9/2005 | Staniforth et al. | 128/203.21 |
| 2003/0044219 A1 | | 3/2003 | Quintero | |
| 2004/0190975 A1 | | 9/2004 | Goodman et al. | |
| 2005/0005934 A1 | * | 1/2005 | Harvey | 128/203.15 |

* cited by examiner

*Primary Examiner*—Kenneth Bomberg
(74) *Attorney, Agent, or Firm*—Frost Brown Todd LLC

(57) ABSTRACT

A multiple use adhesive dispenser facilitates precise, extended dispensing for a surgical procedure by sequentially positioning an ampoule containing a flowable material, such as a polymerizable monomer compound such as a cyanoacrylate adhesive. In one version particularly suited to an open surgical procedure, the ampoules are affixed to a tape substrate that is unreeled from an internal storage reel and transported proximate to an ampoule gripping mechanism with an underlying tape substrate peeled away and internally stored as each ampoule is positioned for dispensing. Actuating an ampoule advancement handle positions the next ampoule and squeezing a movable handle toward a fixed handle effects dispensing. Another version has an elongate shaft that internally augers each ampoule in succession into a pair of spaced jaws that are pinched together by actuating rods to dispense adhesive.

16 Claims, 17 Drawing Sheets

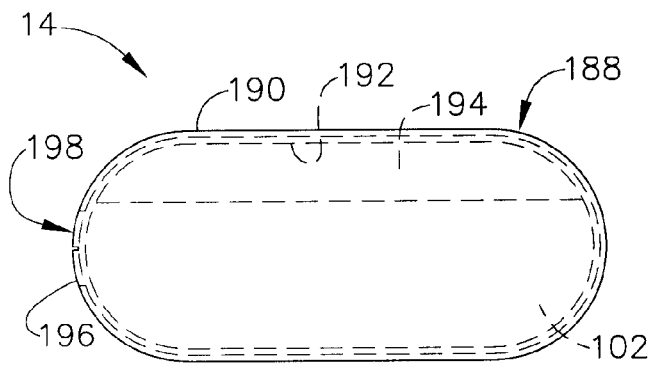 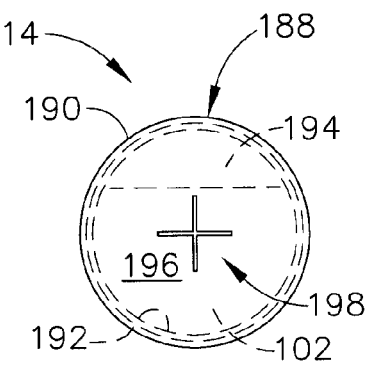
FIG. 14      FIG. 15
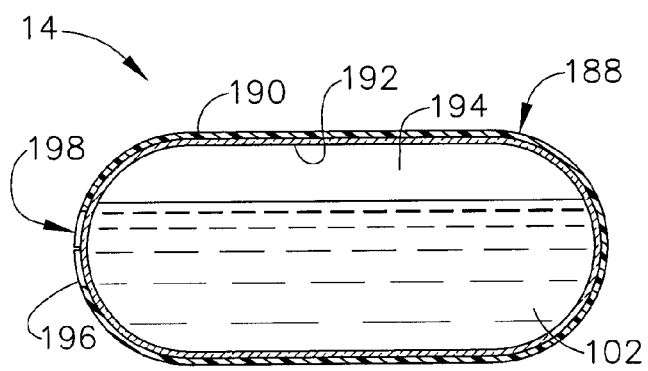
FIG. 16
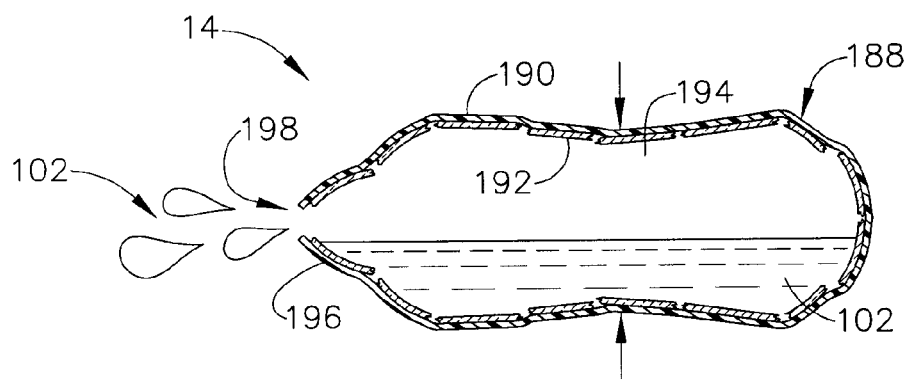
FIG. 17

SURGICAL MULTIPLE USE ADHESIVE APPLIER

REFERENCE TO RELATED APPLICATIONS

The present application is related commonly owned U.S. patent application Ser. No. 11/558,107 "SURGICAL BAND FLUID MEDIA DISPENSER", to Voegele and Hunt filed on even date herewith, the disclosure of which is hereby incorporated by reference in its entirety.

FIELD OF THE INVENTION

This invention relates to applicators and/or dispensers for dispensing and/or applying an adhesive material, for example, a polymerizable monomer compound such as a cyanoacrylate adhesive, particularly for open surgical use and minimally invasive surgical use.

BACKGROUND OF THE INVENTION

Numerous swabs, applicators, dispensers and kits for dispensing and applying various materials, including adhesive materials, are known. However, these known arrangements possess various shortcomings that make them undesirable in many applications.

Monomer and polymer adhesives are used in both industrial (including household) and medical applications. Included among these adhesives are the 1,1-disubstituted ethylene monomers and polymers, such as the X-cyanoacrylates. Since the discovery of the adhesive properties of such monomers and polymers, they have found wide use due to the speed with which they cure, the strength of the resulting bond formed, and their relative ease of use. These characteristics have made the .alpha.-cyanoacrylate adhesives the primary choice for numerous applications such as bonding plastics, rubbers, glass, metals, wood, and, more recently, biological tissues.

Medical applications of 1,1-disubstituted ethylene monomer adhesive compositions include use as an alternate or an adjunct to surgical sutures and staples in wound closure as well as for covering and protecting tissue wounds such as lacerations, abrasions, burns, stomatitis, sores, and other open surface wounds. When such an adhesive is applied, it is usually applied in its monomeric form, and the resultant polymerization gives rise to the desired adhesive bond.

Applicators for dispensing a polymerizable and/or cross-linkable material, such as a 1,1-disubstituted ethylene formulation.

In general, many different 1,1-disubstituted ethylene formulations are known for various applications, for example, cyanoacrylate formulations used as fast-acting surgical adhesives, sealants, bioactive agent release matrixes and implants utilized in medical, surgical and other in vivo applications.

However, due to the need to apply the adhesive in its monomeric form, and due to the rapid polymerization rate of the monomers, it has been very difficult to design effective and commercially viable applicators and/or dispensers. Such applicators and/or dispensers must counterbalance the competing requirements that the monomer not prematurely polymerize, that the monomer be easily applied, that the monomer polymerize at a desired rate upon application, and that the sanitary and/or sterile properties of the monomer and applicator—whether real or perceived—be maintained. This latter requirement, that the actual or perceived sanitary and sterile condition of the monomer and applicator be maintained, is particularly important in medical applications, where the user and/or the patient desires a clean product so as not to introduce further bacteria or foreign matter into a wound site.

Recently, a DERMABOND PROPEN applicator system by CLOSURE MEDICAL CORPORATION, Raleigh, N.C. has become available that dispenses a high viscosity DERMABON™ topical skin adhesive product, available from ETHICON, INC. (Somerville, N.J.). Aspects of such applicators are disclosed in U.S. Pat. Appln. 2004/0190975 A1 "Applicators, dispensers and methods for dispensing and applying adhesive material" to Goodman published 30 Sep. 2004; U.S. Pat. Appln. 2003/0044219 A1 "MICROAPPLICATORS, DELIVERY SYSTEMS AND METHODS FOR ADHESIVES AND SEALANTS" to Quintero published 6 Mar. 2003; and U.S. Pat. No. 6,340,097 to D'Alessio, the disclosures of which are hereby incorporated by reference in their entirety. These applicator systems substantially increase ease of use, adhesive control, expression efficiency, and precision placement over generally known surgical adhesive appliers. However, improvements are yet desired to further enhance these attributes and to incorporate additional advantages.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 14 is a left side view in elevation of the ampoule dispensed by the multiple use adhesive dispenser of FIG. 1 with internal structure and contents depicted in phantom.

FIG. 15 is a front side view in elevation of the ampoule of FIG. 14 depicting an X-shaped perforation in an outer resilient bladder and with internal structure and contents depicted in phantom.

FIG. 16 is a left side view in elevation of the ampoule of FIG. 14 in vertical cross section along a longitudinal axis.

FIG. 17 is a left side view in elevation of the ampoule of FIG. 16 as the ampoule is crushed for dispensing drops of adhesive.

DETAILED DESCRIPTION OF THE INVENTION

Figure 1:
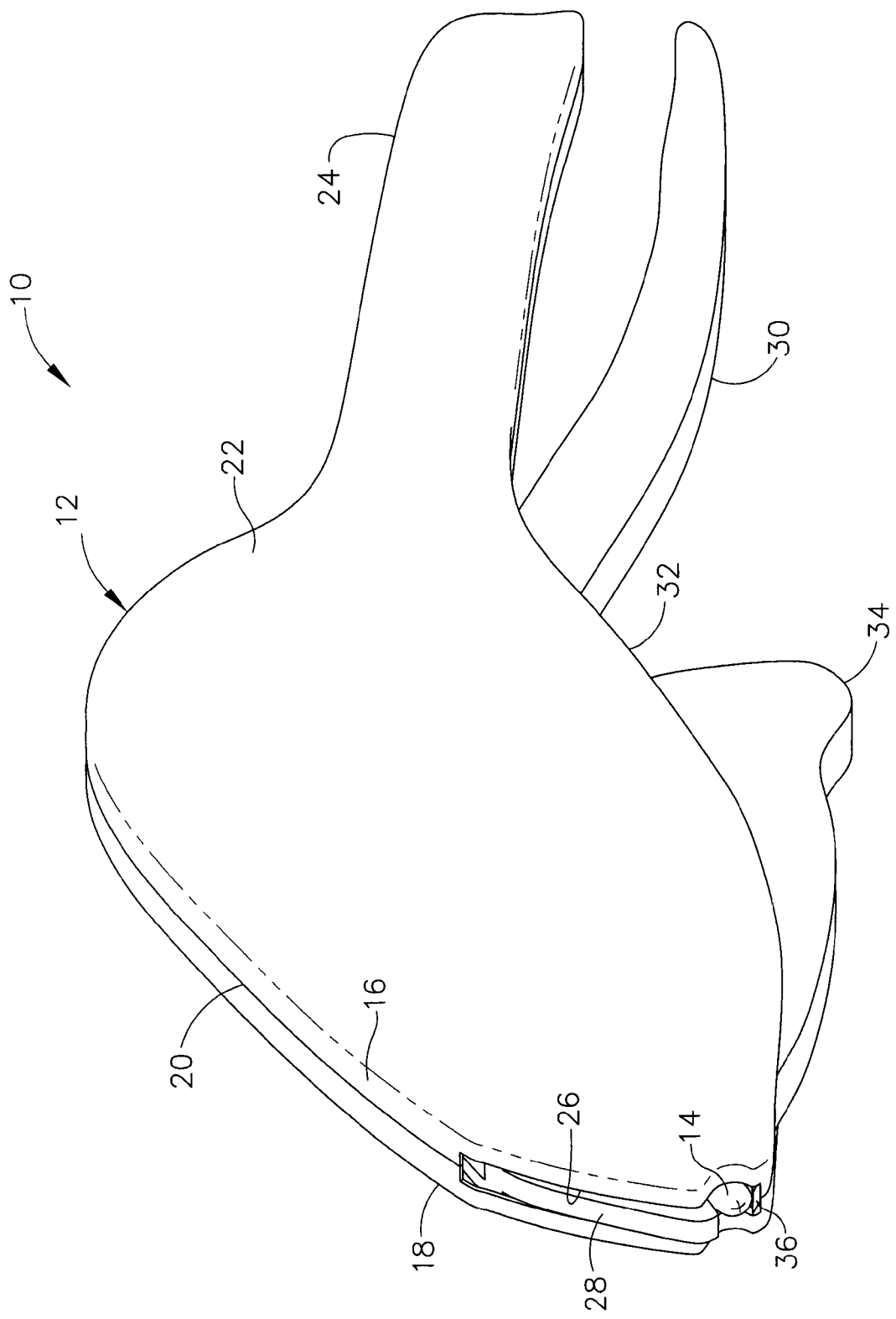
FIG. 1 is a left front isometric view of a multiple use adhesive dispenser for open surgical use that sequentially positions one of a plurality of ampoules each containing an polmerizable adhesive for dispensing.

Turning to the Figures, wherein like numerals denote like components throughout the several views, in FIG. 1, a multiple use adhesive dispenser 10 for open surgical use includes a housing 12 that contains a plurality of frangible ampoules 14 containing an amount of polymerizable adhesive that may be sequentially dispensed so that a single adhesive dispenser 10 may be used repeatedly to dispense discrete amounts of adhesive.

The housing 12 is formed by outwardly laterally symmetric right and left housing half shells 16, 18 joined along an upper seam 20 to form a distal mechanism compartment 22 and a proximal fixed handle 24. A distal vertical rectangular slot 26 is defined between the housing half shells 16, 18 to allow translation of a distal jaw portion 28 within the distal mechanism compartment 22 attached to a proximal movable handle 30 that extends proximally below the proximal fixed handle 24 out of a lower elongate opening 32 also defined between the housing half shells 16, 18. A ratcheting actuator 34 also translates within the lower elongate opening 32. One ampoule 14 at a time is deposited in a generally cylindrically round dispensing channel 36 defined between a lower portion of the distal vertical rectangular slot 26 and the distal jaw portion 28, open distally, and communicating upwardly with the distal vertical rectangular slot 26.

The frangible ampoules 14 may be made of any suitable material, preferably a material that promotes stability and shelf-life of the polymerizable adhesive material. For example, the frangible ampoule 14 may be made of glass. Other materials, such as, a plastic material or pierceable metal, such as aluminum, may be used for the frangible ampoule 14. An example of a suitable ampoule that can be used in the dispenser/applicators of the present invention is disclosed in, for example, U.S. Pat. No. 5,928,611, the entire disclosure of which is incorporated herein by reference. The adhesive dispenser 10 or other versions described herein are particularly suitable for dispensing or applying the adhesive contained in the DERMABON™ topical skin adhesive product, available from ETHICON, INC. (Somerville, N.J.).

Figure 2:
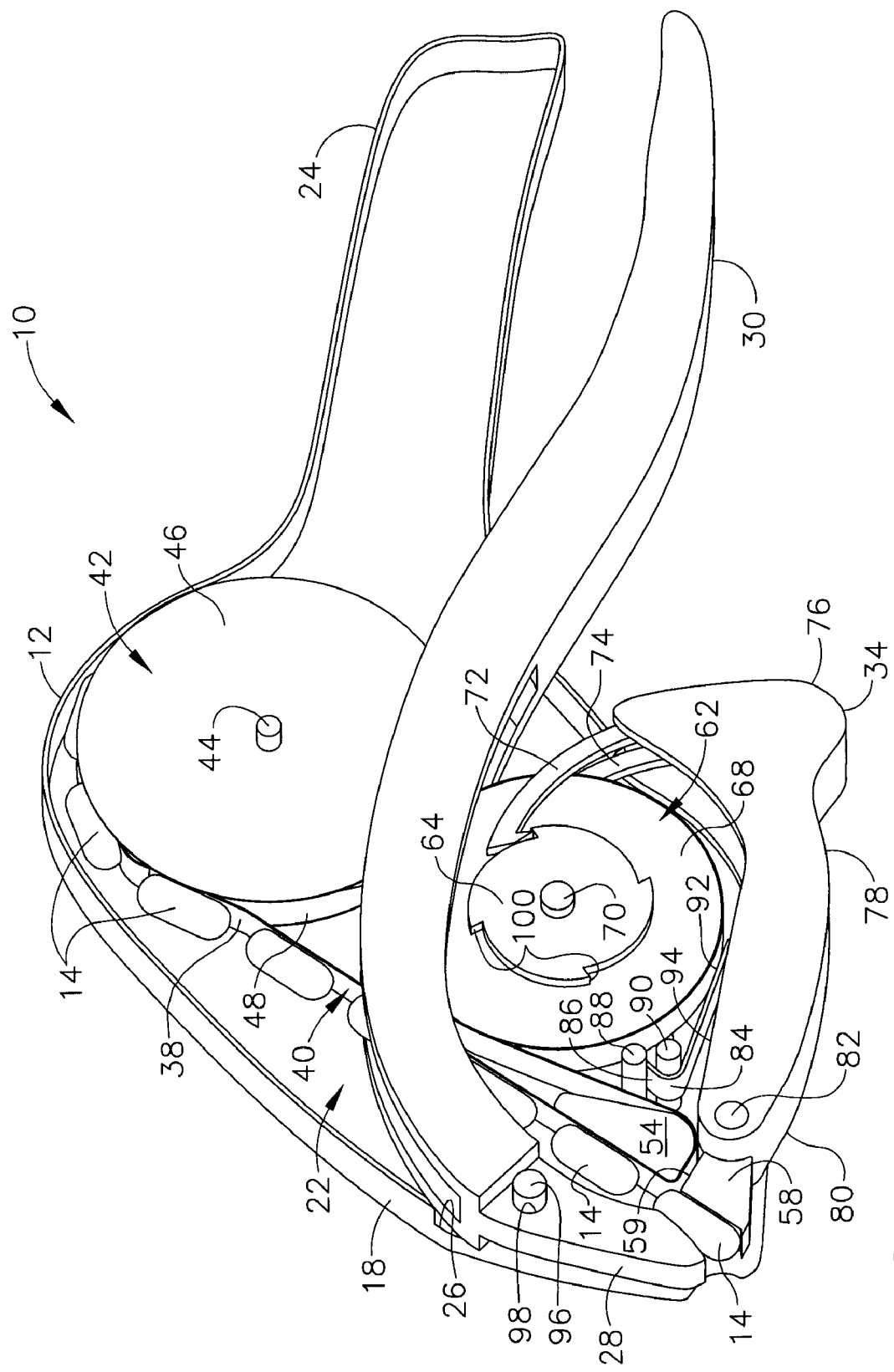
FIG. 2 is a left front isometric view of the multiple use adhesive dispenser of FIG. 1 with a right housing half shell removed to expose mechanisms capable of advancing tape substrate affixed ampoules.
Figure 3:
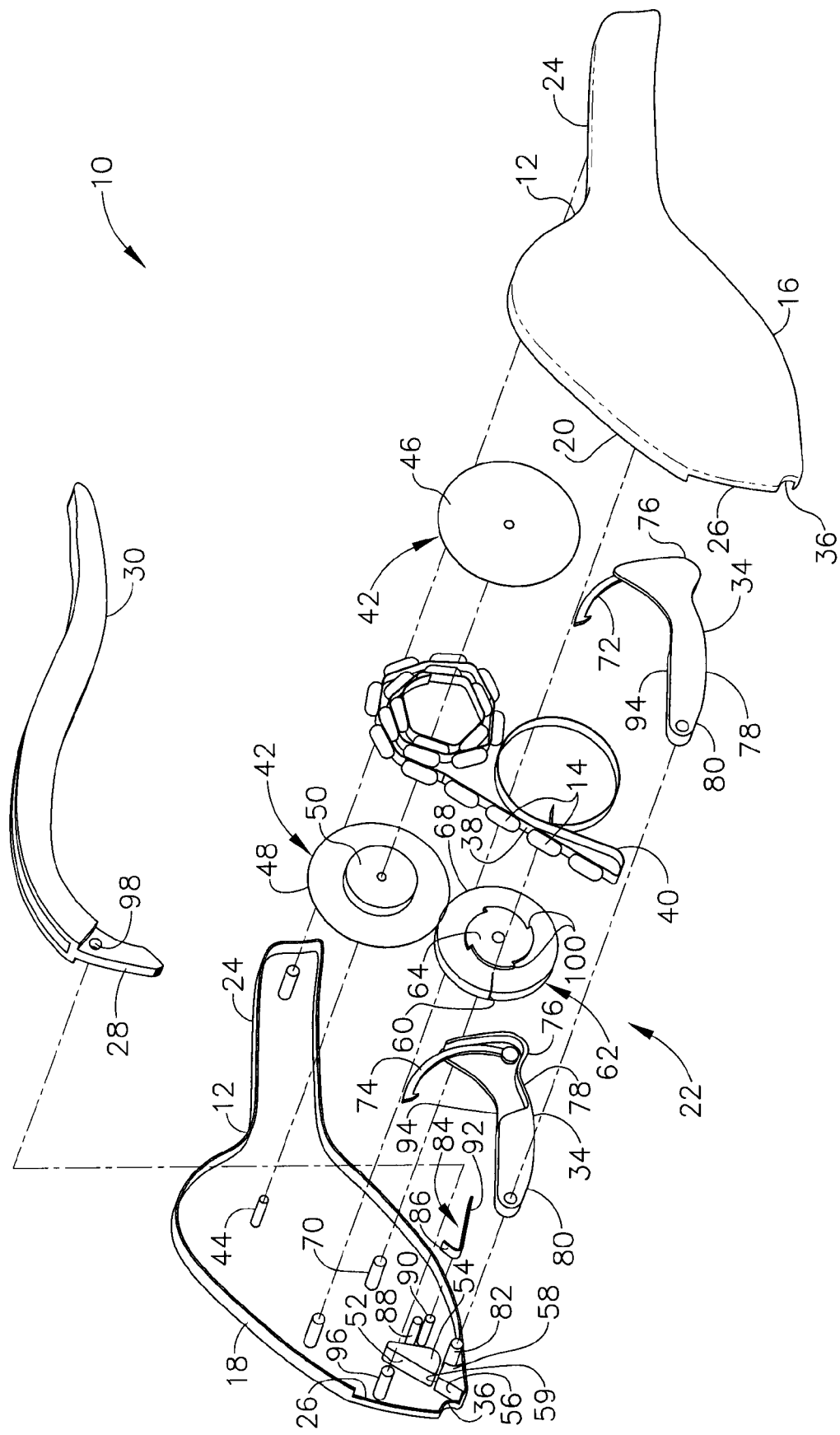
FIG. 3 is a left front exploded view of the multiple use adhesive dispenser of FIG. 1.
Figure 4:
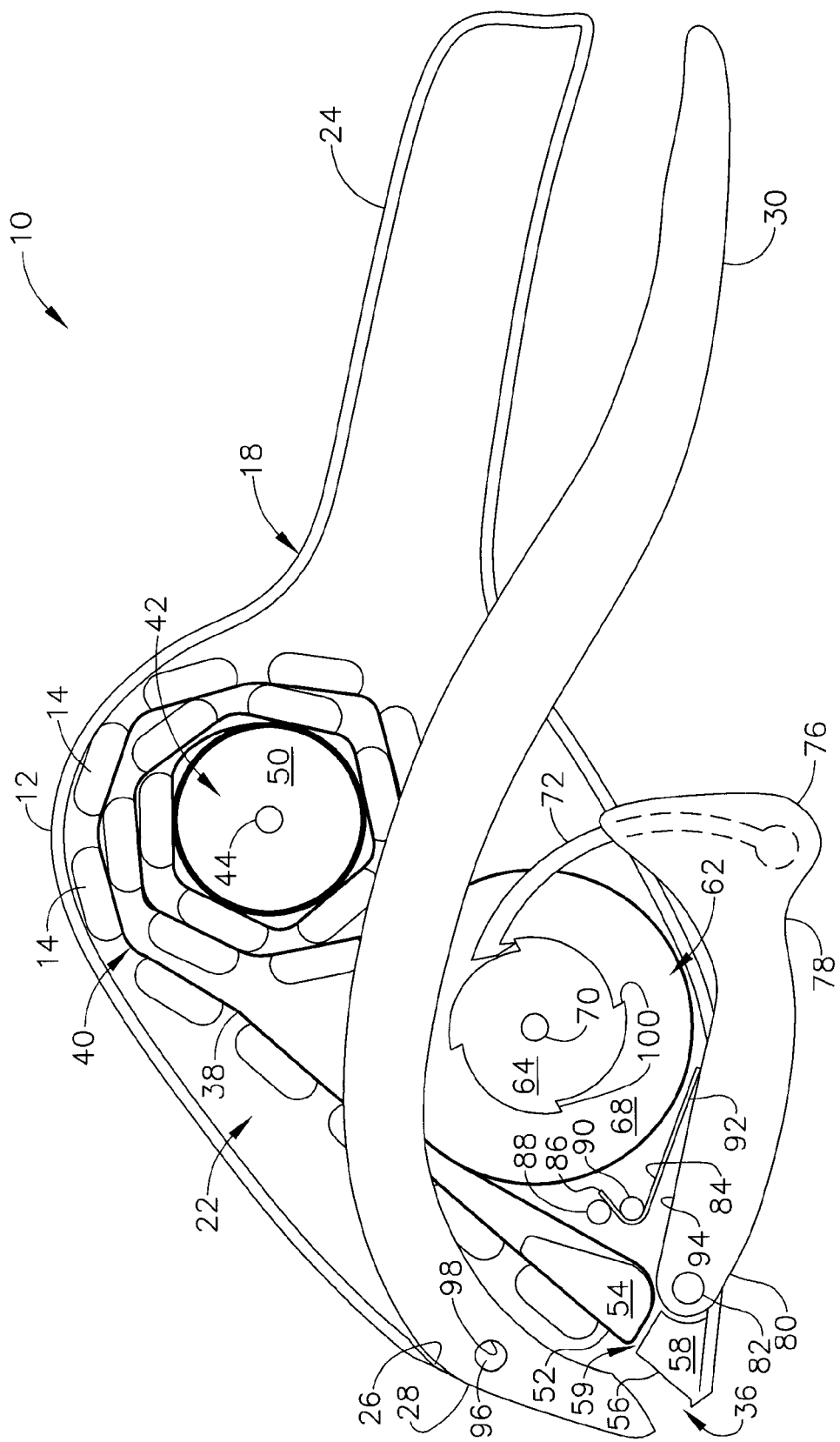
FIG. 4 is a left side view in elevation taken in longitudinal cross section of the multiple use adhesive dispenser of FIG. 1 with an ampoule advancement handle in a lowered, relaxed state.

In FIGS. 2-4, the ampoules 14 are releasably adhered at regular intervals upon a top surface 38 of an elongate dispensing band or tape 40 stored with the top surface 38 outward upon a reel 42 that rotates about a lateral reel axle 44 that extends from the right housing half shell 18 and is engaged to the left housing half shell 16. The reel 42 includes a left disk 46 and a right disk 48 that includes a central hub portion 50. The tape 38 passes over a top surface 52 of a wedge-shaped lateral block 54 aligned with but closely spaced from a top surface 56 of a distal block 58 of the dispensing channel 36 forming a peel-off slot 59, both blocks 54, 58 extending from the right housing half shell 18 and abutting the left housing half shell 16. The close spacing of the peel-off slot 59 between the blocks 54, 58 is sufficient to receive the tape 38 but too narrow for receiving an ampoule 14. The tape 38 passes down the peel-off slot 59 between the blocks 54, 58 and proximally below the wedge shaped lateral block 54, into a radial outer slot 60 formed in a ratcheting take-up wheel 62. Left and right ratchet gears 64 (the latter hidden but identical to the left) extend laterally from each side of a flat cylindrical disk 68 of the ratcheting take-up disk 62 that rotates about a take-up axle 70 laterally extending from the left housing half shell 18 and engaged by the right housing half shell 16.

Each ratchet gear 64 is shaped to engage a top aft moving left and right hook arm 72, 74, respectively, of the ratcheting actuator 34 that curve up and distally from a left and right half of an aft end 76 of an ampoule advancement handle 78 whose distal end 80 pivots about an axle 82 below the wedge shaped lateral block 54 that extends from the right housing half shell 18. A clip spring 84 has a bent end 86 that is captured proximally between closely spaced top and bottom posts 88, 90 that also extend from the right housing half shell 18 proximal to and above the axle 80. A long biasing portion 92 of the clip spring 82 extends downwardly and aft to contact a top surface 94 of the advancement handle 78, biasing the aft end 76 of the advancement handle 78 downwardly. The tape 38 is pulled away from a distal most ampoule 14 that is received between the distal jaw portion 28 and the top surface 56 of the distal block 58 by the tape 38 being rolled onto the ratcheting take-up wheel 62.

Above the wedge-shaped lateral block 54, a handle pivot axle 96 that extends laterally from the right housing half shell 18 passes through a pivot hole 98 formed at a transition between the distal jaw portion 28 and the much longer proximal movable handle 30. The maximum spacing between the distal jaw portion 28 and the distal block 58 is selected such that an ampoule 14 is firmly gripped without crushing when the advancing tape 38 urges an ampoule 14 there between.

Figure 5:
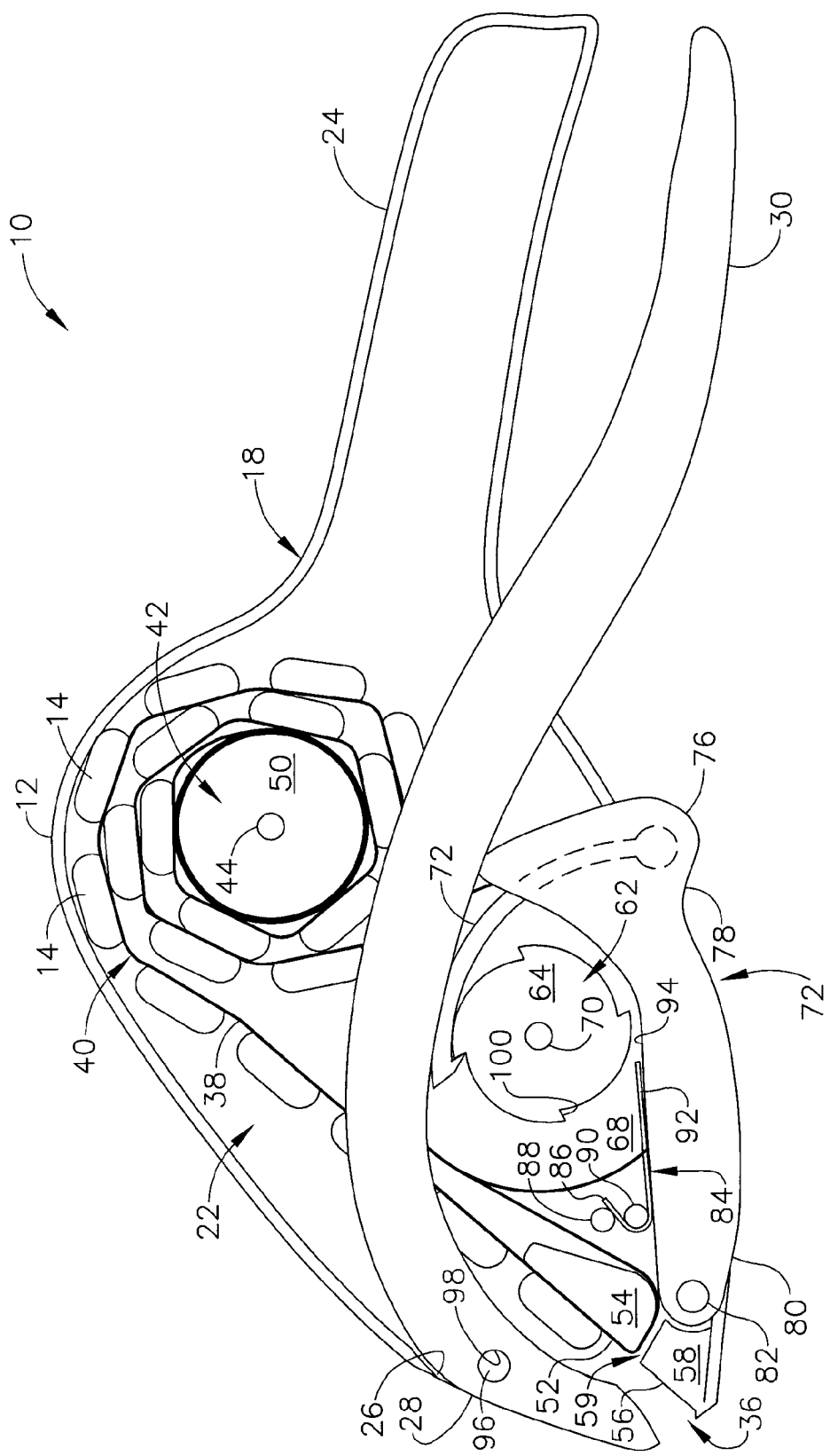
FIG. 5 is a left side view in elevation taken in longitudinal cross section of the multiple use adhesive dispenser of FIG. 4 with the ampoule advancement handle in a raise, actuated state.
Figure 6:
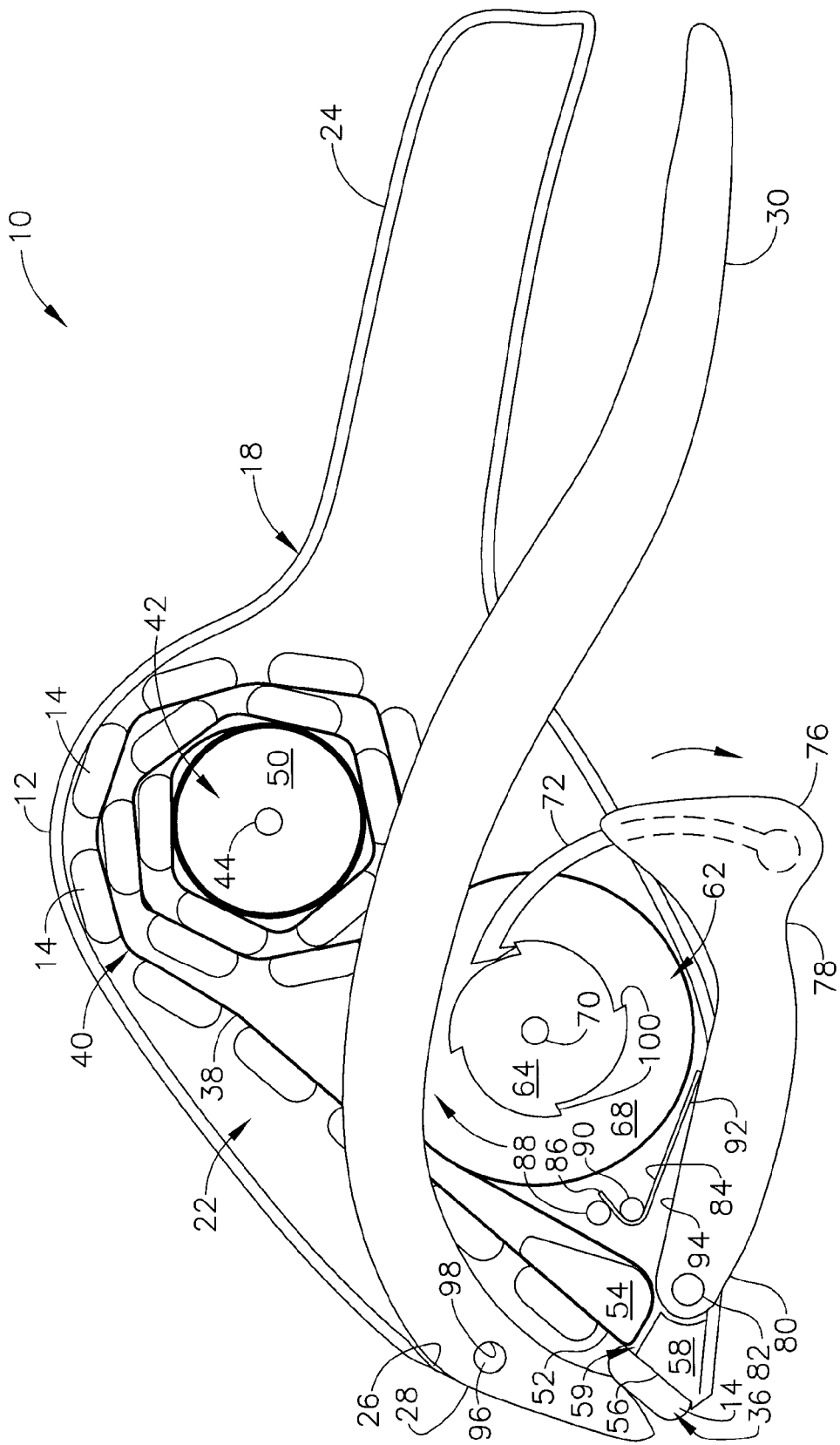
FIG. 6 is a left side view in elevation taken in longitudinal cross section of the multiple use adhesive dispenser of FIG. 5 with an ampoule advancement handle being released back to the lowered, relaxed state, advancing an ampoule into position for dispensing while peeling away and storing an underlying portion of the tape substrate.
Figure 7:
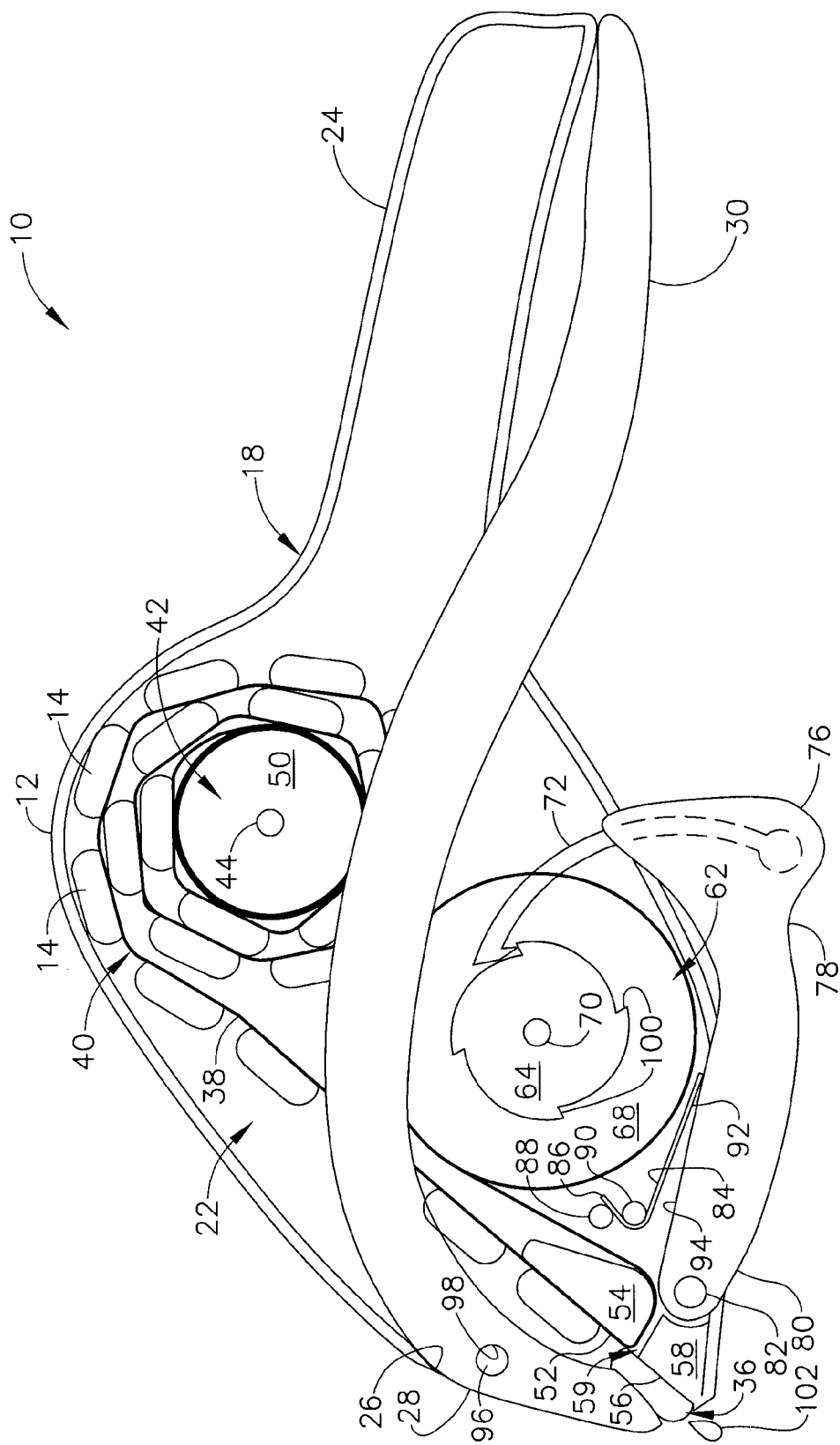
FIG. 7 is a left side view in elevation taken in longitudinal cross section of the multiple use adhesive dispenser of FIG. 6 with a proximal movable handle raised toward a proximal fixed handle to dispense adhesives by crushing the distal most ampoule.

In FIG. 5, the ampoule advancement handle 94 has been manually pushed upward into the distal mechanism compartment 22 such that the hook arms 72, 74 move approximately a quarter turn around the ratchet gears 64 to reengage another ratchet tooth 100. In FIG. 6, the ampoule advancement handle 94 is released, allowing the clip spring 84 to rotate the handle 94 downward, thereby rotating the ratcheting take-up wheel 62 to reel up an additional interval of tape 38. In FIG. 7, the movable handle 30 has been squeezed against the fixed handle 24, causing an ampoule 14 to be crushed, dispensing adhesive drops 102.

In FIGS. 10-13, an alternative multiple use adhesive dispenser 110 for minimally invasive surgical use has an elongate shaft 112 for passing endoscopically through a body orifice (e.g., throat) or laparoscopically through a surgical access (e.g., incision, trocar) (not shown). The shaft 112 comprises an outer tube 114 that may be rigid, flexible or deformable. The shaft 112 is connected proximally to a rotation knob 116 that in turn is coupled for rotation to a handle 118. The shaft 112 is distally connected to an end effector, depicted as an upper and a lower jaw 120, 122 configured to move between a parallel spaced orientation ("open") to receive an ampoule 14 and a distally pinched orientation ("closed" or "dispensing"). A clinician grasps the handle 118 by inserting a thumb into a thumb ring 124 of an upper pivoting trigger 126 and a first two fingers into a finger ring 128, which is forward and slightly below of the thumb ring 124 and which is part of a lower fixed member 130 that projects downwardly from a barrel portion 132 attached to the rotation knob 116 and shaft 112. In response to actuating the upper pivoting trigger 126 toward the lower fixed member 130, distal ends of the jaws 120, 122 are pinched together, crushing the ampoule 14. Retracting the upper pivoting trigger 126 advances another ampoule 14 into the opened jaws 120, 122.

Figure 10:
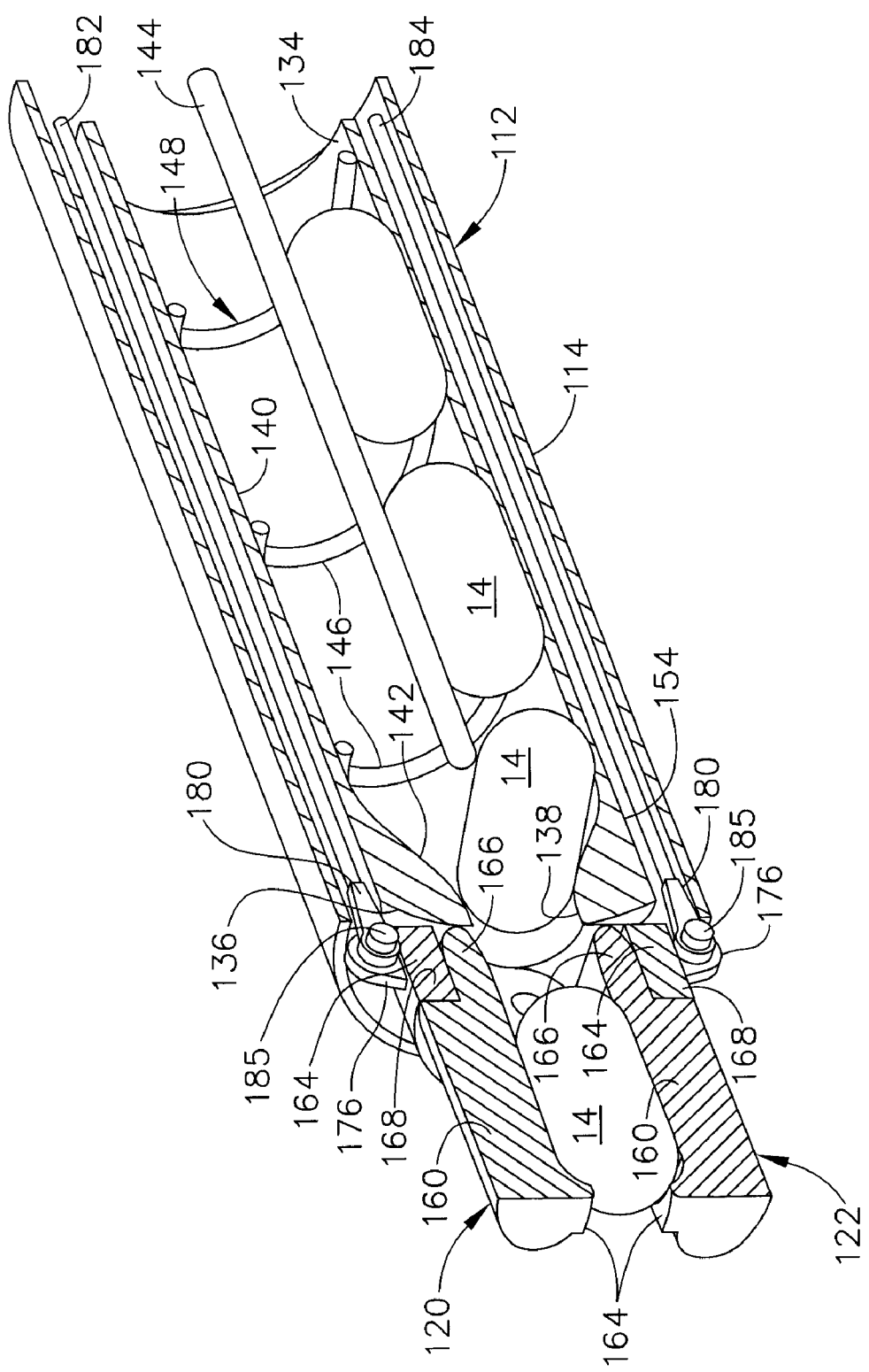
FIG. 10 is a left front isometric view of the distal portion of the alternative multiple use adhesive dispenser of FIG. 9 taken in vertical cross-section along a longitudinal axis to expose the plurality of ampoules being positioned for sequential dispensing.
Figure 11:
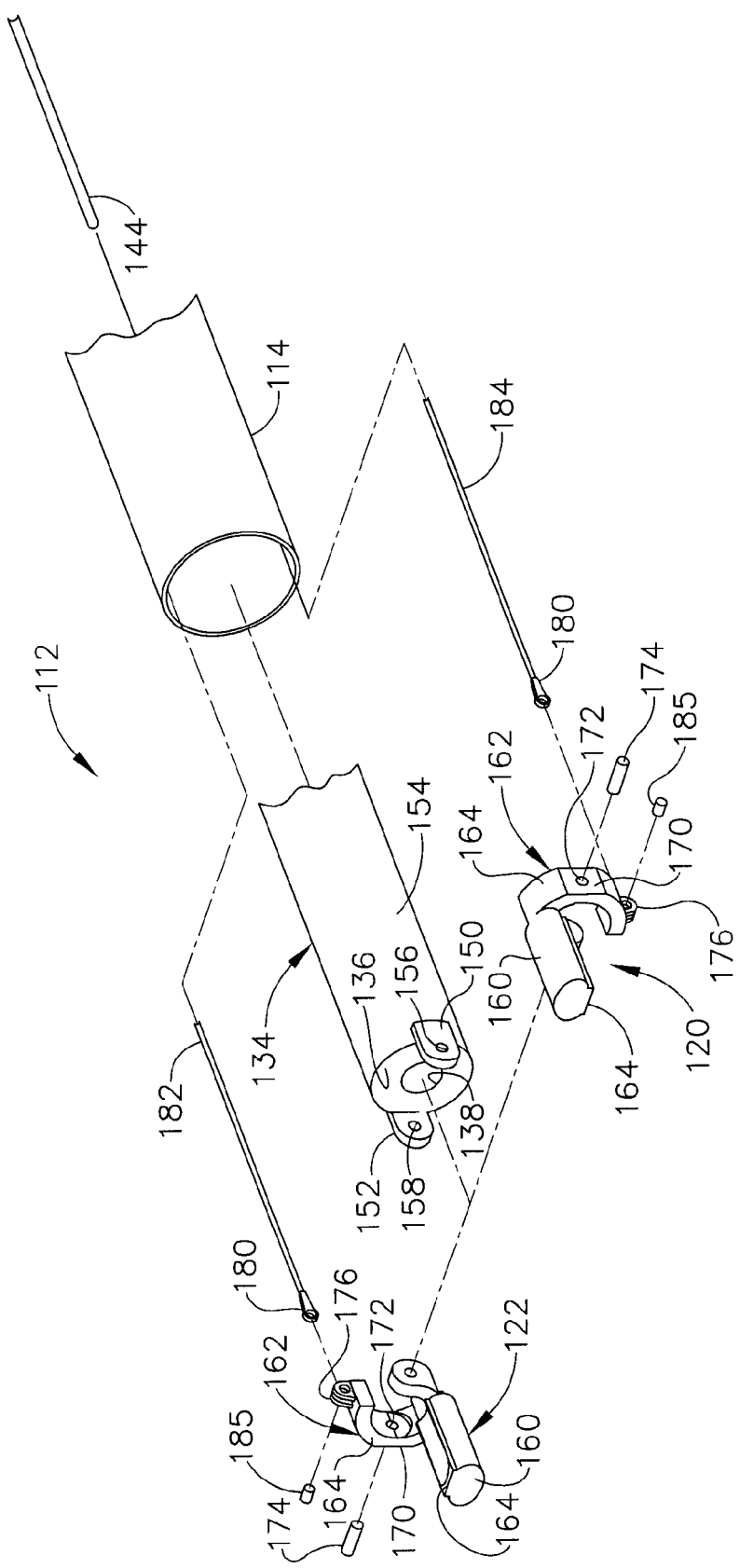
FIG. 11 is a left front exploded view of the distal portion of the alternative multiple use adhesive dispenser of FIG. 8.

The shaft 112 includes a generally cylindrical elongate frame 134 that is received within the outer tube 114. A distal end 136 of the frame 134 includes a central hole 138 slightly larger than a lateral diameter of the ampoules 14. With particular reference to FIG. 10, an internal cylindrical cavity 140 of the frame 134 has an internal diameter slightly larger than twice the lateral diameter of the ampoules 14 and transitions distally to a tapered nozzle portion 142 down distally to the central hole 138. An ampoule guide rod 144 extends from a proximal connection (not shown) to the handle 118 down a longitudinal center axis of the frame 134 and outer tube 114, urging each sequentially lined up ampoule 14 between coils 146 of an advancement spring 148 closely sized to the internal cylindrical cavity 140. For the depicted orientation of the coils 146, counterclockwise rotation of the advancement spring 148, as viewed from a distal orientation, urges the ampoules 14 distally. The ampoule guide rod 144 distally terminates prior to the tapered nozzle portion 142, allowing each ampoule 14 in turn to ramp inwardly through the central hole 138 to be received by the jaws 120, 122. A left and a right mounting tab 150, 152 are attached to an outer circumference 154 proximate to the distal end 136 of the frame 134, oriented on opposite sides of the central hole 138 and projecting further distally to present respective left and right pivot holes 156, 158 for pivotal mounting of the jaws 120, 122.

Figure 9:
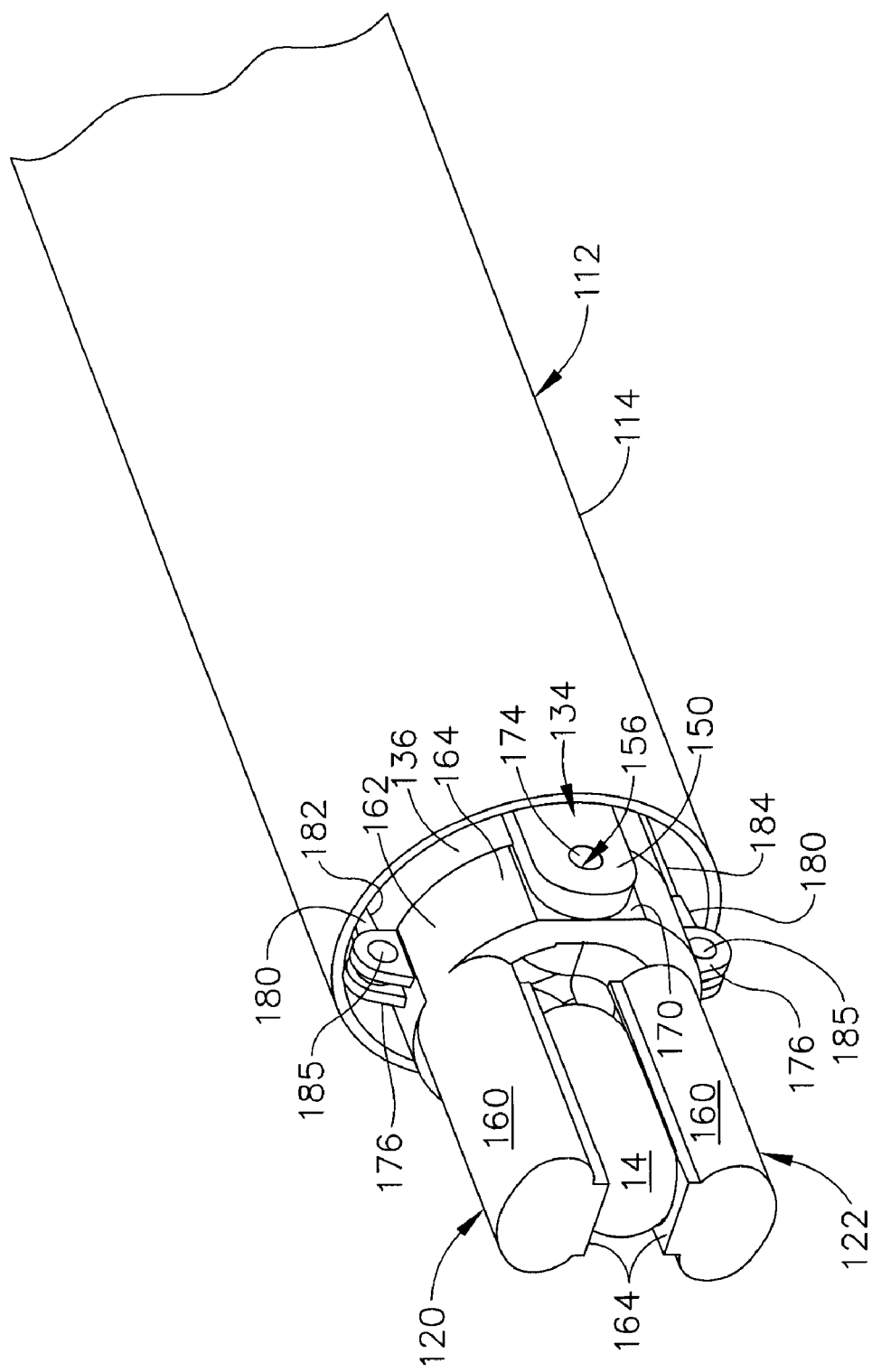
FIG. 9 is a left front isometric view of a distal portion of the alternative multiple use adhesive dispenser of FIG. 8.

With particular reference to FIG. 10, each jaw 120, 122 is identical to the other and assembled with one jaw 120 rotated 180° about the longitudinal axis relative to the other jaw 122. Each jaw 120, 122 has a distally extending anvil portion 160 that is positioned by a jaw mounting portion 162 to reside approximately between the outer circumference 154 and the central hole 138 of the frame 134 (i.e., above and below respectively for jaws 120, 122). Each anvil portion 160 has a flat inner surface 163 that transitions to a small, inwardly ramped distal portion 164 to capture the distal most ampoule 14 (FIGS. 9-10). Each mounting portion 162 comprises a half cylindrical band 165 attached at one counterclockwise end 166 (as viewed from a distal orientation) to a proximal surface of the anvil portion 160 wrapping clockwise around and distal to the central hole 138 as viewed from a distal position to a free clockwise end 168. An outer flattened surface 170 midway around the half cylindrical band 165 between the counterclockwise and clockwise ends 166, 168 has a side pivot hole 172 that is positioned inside of a respective mounting tab 156, 158 and is rotatably attached by a pivot pin 174. The free clockwise end 168 has an outwardly extending, transversely aligned clevis 176 that receives a distal eyelet end 180 of a respective upper and lower actuating rod 182, 184, which are held therein by a respective clevis pin 185, each actuating rod 182, 184 received for longitudinal translation between the outer tube 114 and the frame 134 to communicate a closing motion from the handle 118.

Figure 12:
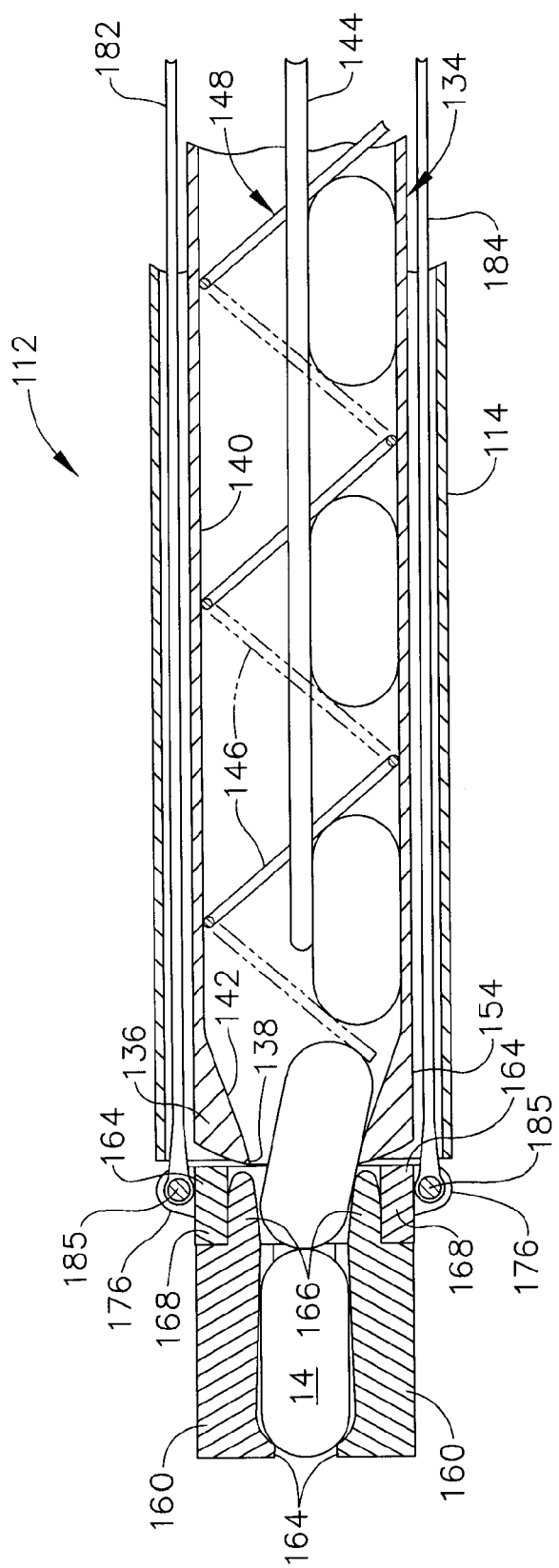
FIG. 12 is a left side view in elevation of the distal portion of the alternative multiple use adhesive dispenser of FIG. 9 taken in vertical cross-section along a longitudinal axis to expose the plurality of ampoules being positioned for sequential dispensing.
Figure 13:
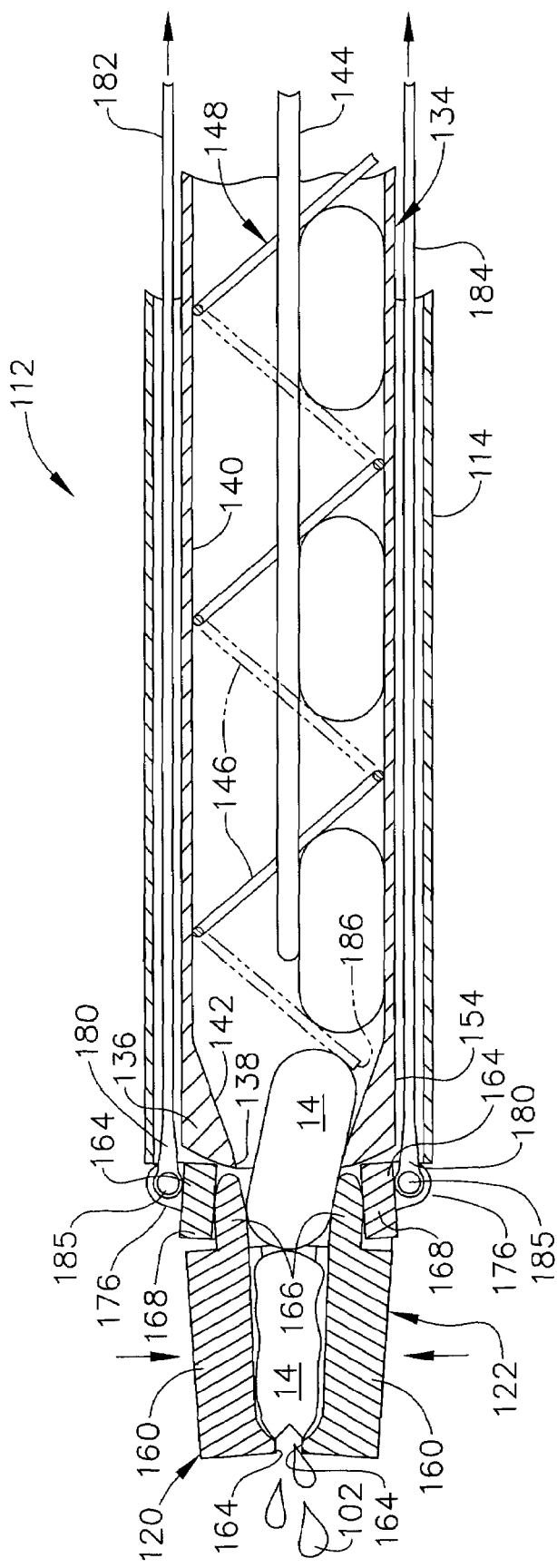
FIG. 13 is a left side view in elevation of the distal portion of the alternative multiple use adhesive dispenser of FIG. 12 taken in vertical cross-section along a longitudinal axis to expose the plurality of ampoules being positioned for sequential dispensing and a distal most ampoule being crushed between an upper and a lower jaw.
Figure 18:
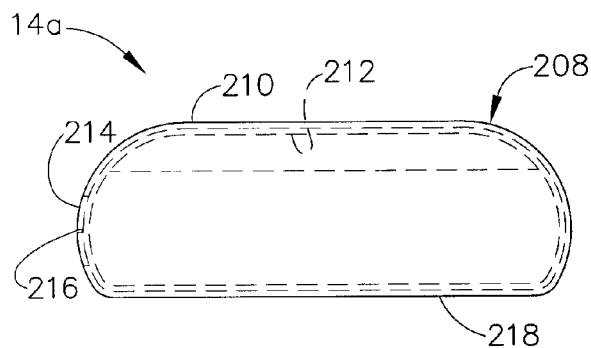
FIG. 18 is a left side view of an alternative ampoule with internal structure and contents depicted in phantom and a flat bottom surface for dispensing by the multiple use adhesive dispenser of FIG. 8.

In FIG. 12, action by a distal termination 186 of the advancement spring 148 is brushing a proximal end of an ampoule 14 that is partially extending through the central hole 138, preventing a distal most ampoule 14 within the jaws 120, 122 from retracting. In FIG. 13, the upper and lower actuating rods 182, 184 are longitudinally advanced, causing the upper and lower jaws 120, 122 to rotate inwardly about their side pivot holes 172 that are connected to the frame 134 of the shaft 114 (FIG. 9). Thereby, the ampoule 14 is crushed, ejecting drops of adhesive 102.

In FIGS. 14-17, the ampoule 14 is depicted as having a composite containment structure 188 comprised of an outer resilient bladder 190 that closely encompasses a frangible capsule 192 that contains a quantity of adhesive 102 and air 194. In FIG. 15, a distal end 196 of the outer resilient bladder 190 has an X-shaped perforation 198. In FIG. 17, lateral compression of the ampoule 14 within the multiple use adhesive dispenser 10 (FIG. 1) causes the frangible capsule 192 to fracture with the fluid pressure directed by bladder 196 to the X-shaped perforation 198, resulting in rupture and the ejection of droplets of adhesive 102.

Figure 8:
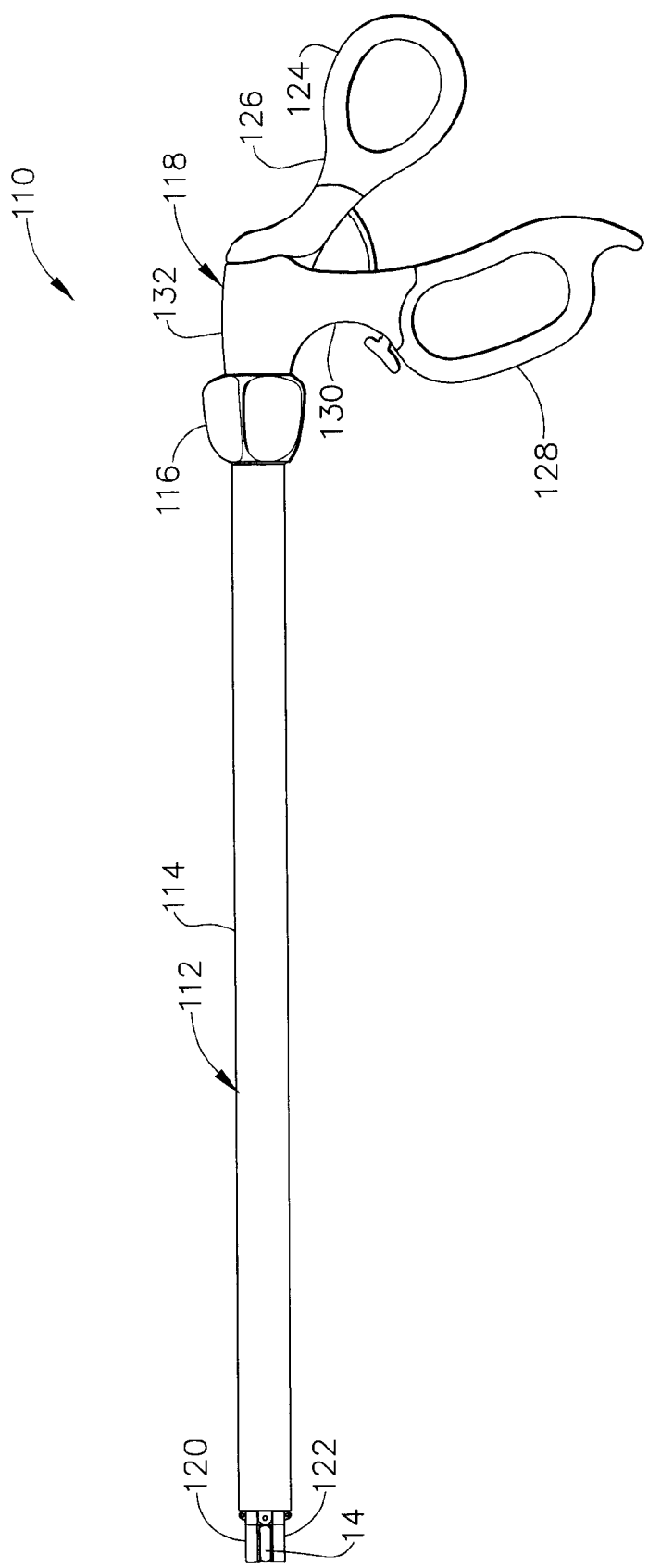
FIG. 8 is a left side view in elevation of an alternative multiple use adhesive dispenser for a minimally invasive surgical procedure that sequentially positions one of a plurality of ampoules each containing a polmerizable adhesive for dispensing.
Figure 19:
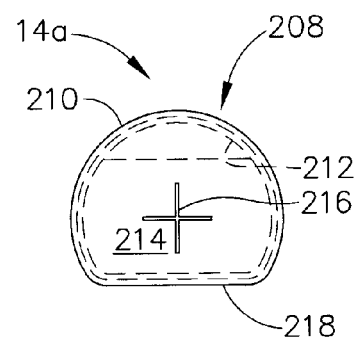
FIG. 19 is front side view in elevation of the alternative ampoule of FIG. 18 depicting an X-shaped perforation in an outer resilient bladder and with internal structure and contents depicted in phantom.
Figure 20:
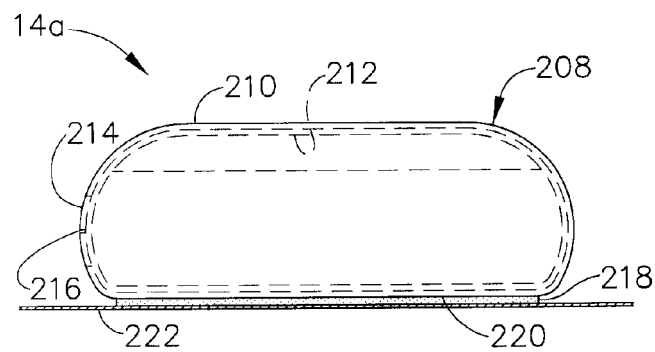
FIG. 20 is a left side view of the alternative ampoule of FIG. 18 with internal structure and contents depicted in phantom and releasably adhesively affixed to a tape substrate.
Figure 21:
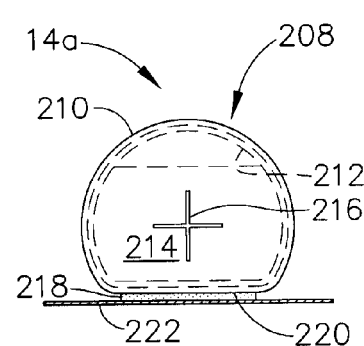
FIG. 21 is a front side view in elevation of the alternative ampoule of FIG. 20 with internal structure and contents depicted in phantom and releasably adhesively affixed to the tape substrate.

In FIGS. 18-21, an alternative ampoule 14*a* is depicted as having a flat bottom composite containment structure 208 comprised of an outer resilient bladder 210 that closely encompasses a frangible capsule 212 that contains a quantity of adhesive 102 and air 194. In FIG. 19, a distal end 214 of the outer resilient bladder 210 has an X-shaped perforation 216. A releasable adhesion layer 218 holds a flat bottom surface 220 of the composite containment structure 208 to a tape substrate 222 for use in the multiple use adhesive dispenser 110 (FIG. 8) or similar devices.

Figure 22:
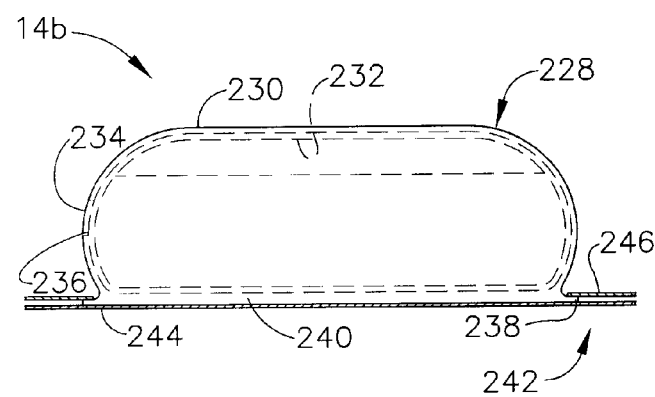
FIG. 22 is a left side view of another alternative ampoule with internal structure and contents depicted in phantom and a mounting flange integral to an outer resilient bladder sandwiched into a composite tape substrate for dispensing by the multiple use adhesive dispenser of FIG. 8.
Figure 23:
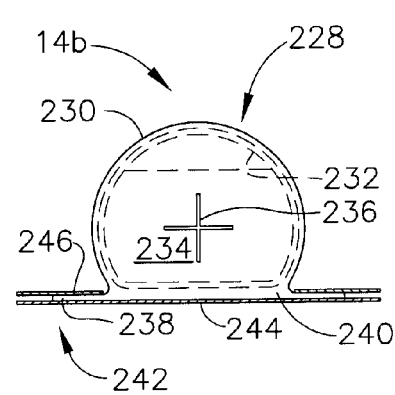
FIG. 23 is a front side view of the another alternative ampoule of FIG. 22 depicting an X-shaped perforation and with internal structure and contents depicted in phantom.

In FIGS. 22-23, another alternative ampoule 14b is depicted as having a flat bottom composite containment structure 228 comprised of an outer resilient bladder 230 that closely encompasses a frangible capsule 232 that contains a quantity of adhesive 102 and air 194. In FIG. 23, a distal end 234 of the outer resilient bladder 230 has an X-shaped perforation 236. The outer resilient bladder 230 includes a releasable mounting flange 238 that extends horizontally around a flat bottom surface 240 of the composite containment structure 208. A composite tape substrate 242 for use in the multiple use adhesive dispenser 110 (FIG. 1) or similar devices has a lower substrate 244 upon which the flat bottom surface 240 and releasable mounting flange 238 are placed. An upper substrate 246 affixed to the lower substrate 244 surrounds the ampoule 14b and releasably holds down the releasable mounting flange 238.

Figure 24:
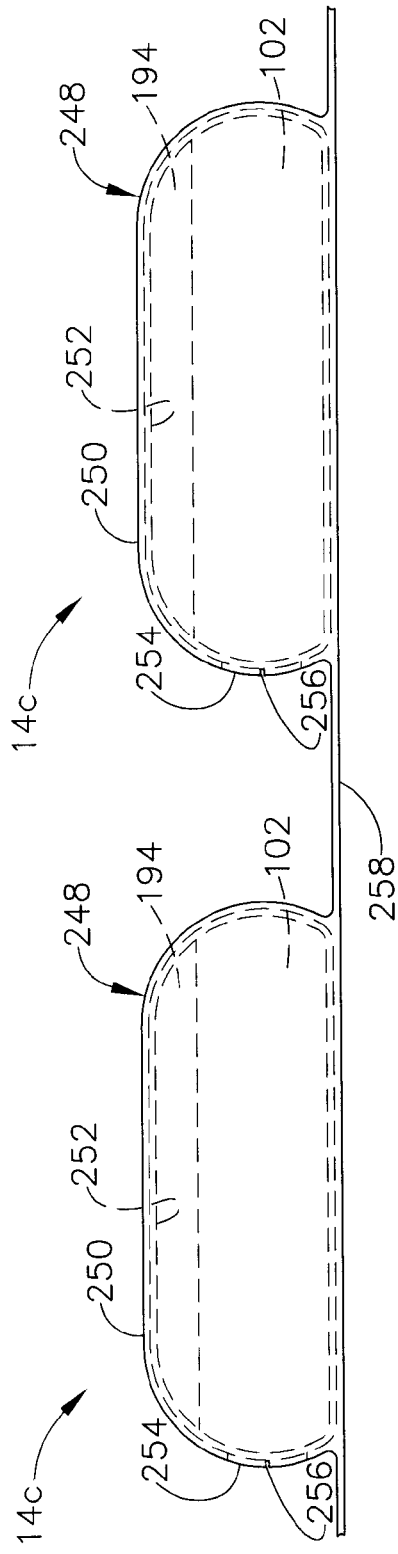
FIG. 24 is a left side view of two additional alternative ampoules with internal structure and contents depicted in phantom and with an outer resilient bladder around each ampoule extending between ampoules as a tape substrate for dispensing by the multiple use adhesive dispenser of FIG. 8.
Figure 25:
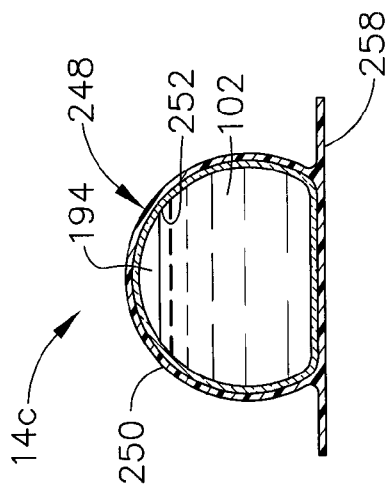
FIG. 25 is a front side view of one of the additional alternative ampoules of FIG. 24 in vertical cross section.

In FIGS. 24-25, an additional alternative ampoule 14c is depicted as having a flat bottom composite containment structure 248 comprised of an outer resilient bladder 250 that closely encompasses a flat bottomed frangible capsule 252 that contains a quantity of adhesive 102 and air 194. A distal end 254 of the outer resilient bladder 250 has an X-shaped perforation 256. The same resilient material that encompasses the frangible capsule 252 extends between ampoules 14c to form an integral tape substrate 258 for use in the multiple use adhesive dispenser 110 (FIG. 1) or similar devices.

Figure 26:
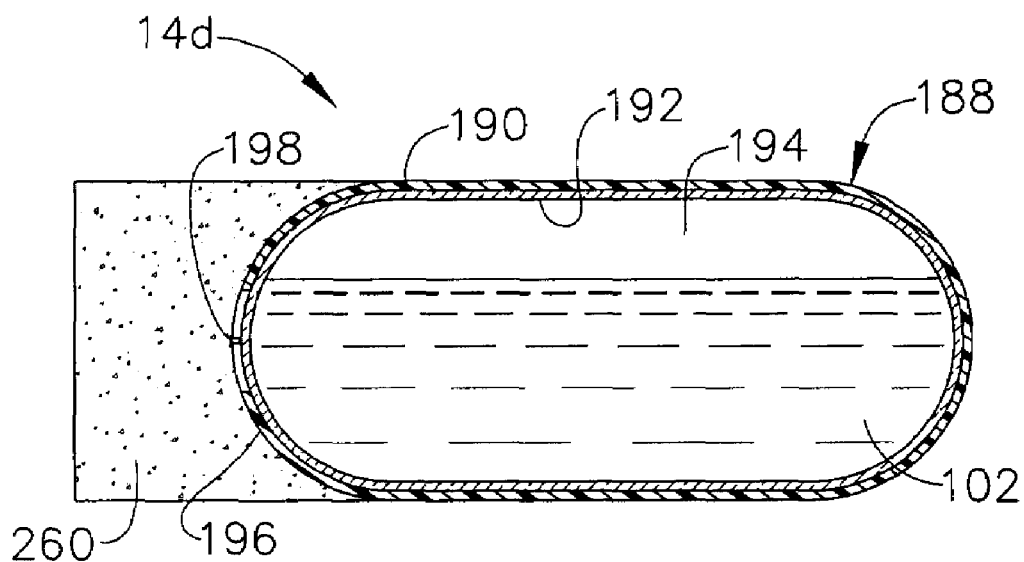
FIG. 26 is a left side view in vertical cross section along a longitudinal axis of a further alternative ampoule having a distal foam applicator tip.
Figure 27:
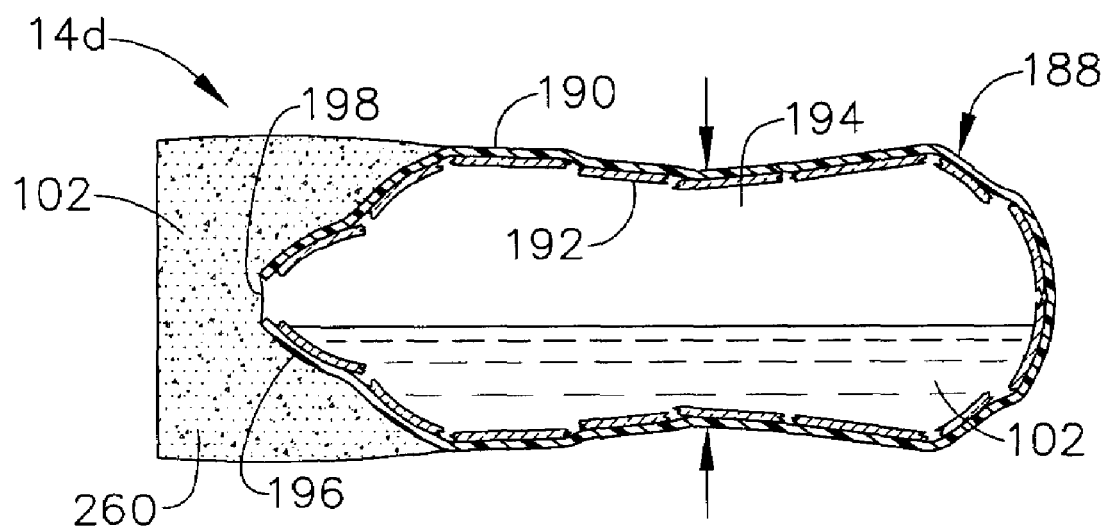
FIG. 27 is a left side view in vertical cross section along the longitudinal axis of the further alternative ampoule of FIG. 26 during dispensing.

In FIGS. 26-27, a further alternative ampoule 14d is depicted as having the composite containment structure 188 comprised of the outer resilient bladder 190 that closely encompasses a frangible capsule 192 that contains a quantity of adhesive 102 and air 194. The distal end 196 of the outer resilient bladder 190 has an X-shaped perforation 198. A foam applicator tip 260 covers the distal end 196 and extends distally. In FIG. 27, lateral compression of the ampoule 14d within the multiple use adhesive dispenser 10 (FIG. 1) causes the frangible capsule 192 to fracture with the fluid pressure directed by bladder 196 to the X-shaped perforation 198, resulting in rupture and the ejection of droplets of adhesive 102 into the foam applicator tip 260.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, rather than a polymerizable monomer compound such as a cyanoacrylate adhesive, a two-part adhesive may be incorporated into an ampoule, separated by a frangible barrier that allows mixing during dispensing.

As another example, a plurality of ampoules may remain affixed to a tape substrate with the crushed ampoule and underlying tape substrate being reeled into storage after dispensing.

As an additional example, rather than pushing the opposing jaws closed with actuating rods, reduction in a diameter of a minimally invasive surgical instrument may be realized by changing the jaws such that pulling may effect closing, thus additional force through an actuation member capable of additional force in tension than compression may allow a smaller mechanization.

As yet a further example, while a spring and a guide rod are illustrative of an augering advancement of individual ampoules, applications consistent with the present may employ other distally moving mechanisms such as a Archimedes screw, a conveyor belt with engagement compartments, etc.

What is claimed is:

1. A surgical dispenser, comprising:
a plurality of ampoules, each ampoule containing a adhesive;
a housing comprising a fixed handle, wherein the housing contains the plurality of ampoules and defines an elongate opening;
an ampoule gripping mechanism comprising a pivotally moveable handle comprising a proximal end and a distal end, wherein the proximal end extends out of the elongate opening defined by the housing, and wherein the moveable handle is positionable in relation to the fixed handle of the housing between an open state to receive a selected one of the plurality of ampoules at the distal end and a closed state compressing the selected ampoule to dispense the adhesive; and
an actuator, wherein the actuator is pivotally attached to the housing, and wherein the actuator is operably configured to position the selected one of the plurality of ampoules at the distal end of the moveable handle into the ampoule gripping mechanism; wherein the movable handle and the actuator are movable independently relatively to each other.

2. The surgical dispenser of claim 1, further comprising a tape substrate for positioning the plurality of ampoules and ampoules; wherein the actuator is operable to advance the tape substrate off of the reel to position the selected one of the plurality of ampoules at the distal end of the movable handle into the ampoule gripping mechanism and a reel rotatably contained within the housing to store the tape substrate.

3. The surgical dispenser of claim 2, further comprising a take-up wheel for storing at least the tape substrate.

4. The surgical dispenser of claim 2, further comprising at least one block operably configured to separate the tape substrate from the selected one of the plurality of ampoules.

5. The surgical dispenser of claim 2, wherein each ampoule comprises a frangible capsule containing the adhesive and a resilient bladder, wherein the resilient bladder encompasses the frangible capsule and comprises a perforation for directing the adhesive released during compression of the frangible capsule for dispensing.

6. The surgical dispenser of claim 5, wherein the frangible capsule comprises a flat bottom surface coated by the resilient bladder that is adhered to the tape substrate.

7. The surgical dispenser of claim 5, wherein the frangible capsule comprises a flat bottom surface coated by the resilient bladder forming a laterally flanged flat surface that is sandwiched onto the tape substrate.

8. The surgical dispenser of claim 5, wherein the frangible capsule comprises a flat bottom surface coated by the resilient bladder, the tape substrate comprising an extension of resilient material that forms the resilient bladder.

9. The surgical dispenser of claim 1, wherein the adhesive comprises a polymerizable monomer.

10. The surgical dispenser of claim 9, wherein the polymerizable monomer adhesive comprises a cyanoacrylate adhesive.

11. The surgical dispenser of claim 1, further comprising a foam applicator portion attached to each ampoule.

12. A surgical dispenser, comprising:
a plurality of ampoules encompassing adhesive, the plurality of ampoules being sequentially supported by an elongate substrate;
a housing comprising a fixed handle, wherein the housing stores the plurality of ampoules and defines an opening;
an ampoule gripping mechanism comprising a pivotally moveable handle comprising a proximal end and a distal end, wherein the proximal end extends out of the opening defined by the housing, and wherein the moveable handle is positionable between an open state to receive a selected one of the plurality of ampoules at the distal end and a closed state compressing the selected ampoule to dispense the adhesive; and
an actuator, the actuator pivotally attached to the housing, and wherein the actuator is operably configured to position the elongate substrate to sequentially place the selected one of the plurality of ampoules at the distal end of the moveable handle into the ampoule gripping mechanism; wherein the movable handle and the actuator are movable independently relatively to each other.

13. The surgical dispenser of claim 12, further comprising:
a storage reel contained in the housing holding a length of the elongate substrate that supports the plurality of ampoules;
at least two blocks internally disposed in the housing, wherein the at least two blocks define a slot proximate to the distal end of the moveable handle and through which a length of the elongate substrate can be directed proximate to the ampoule gripping mechanism;
a take-up wheel to receive the elongate substrate from the at least two blocks;
wherein the actuator is operably configured to rotate the take-up wheel in a pulling direction.

14. The surgical dispenser of claim 12, wherein the adhesive comprises a polymerizable monomer.

15. The surgical dispenser of claim 14, wherein the polymerizable monomer adhesive comprises a cyanoacrylate adhesive.

16. The surgical dispenser of claim 12, further comprising a foam applicator portion attached to each ampoule.

* * * * *